United States Patent
Reinke

(10) Patent No.: US 8,239,025 B2
(45) Date of Patent: Aug. 7, 2012

(54) SYSTEM AND METHOD FOR THE REMOTE PROGRAMMING OF A PERSONAL MEDICAL DEVICE

(75) Inventor: Joachim Reinke, Berlin (DE)

(73) Assignee: BIOTRONIK CRM Patent AG (CH)

( * ) Notice: Subject to any disclaimer, the term of this patent is extended or adjusted under 35 U.S.C. 154(b) by 1093 days.

(21) Appl. No.: 12/134,484

(22) Filed: Jun. 6, 2008

(65) Prior Publication Data

US 2009/0030472 A1    Jan. 29, 2009

(30) Foreign Application Priority Data

Jul. 28, 2007    (DE) .......................... 10 2007 035 534

(51) Int. Cl.
*A61N 1/02* (2006.01)
(52) U.S. Cl. .......................................................... 607/30
(58) Field of Classification Search ................. 607/2, 30
See application file for complete search history.

(56) References Cited

U.S. PATENT DOCUMENTS

| | | |
|---|---|---|
| 6,442,433 B1 | 8/2002 | Linberg |
| 6,880,085 B1 | 4/2005 | Balczewski et al. |
| 7,096,067 B2 | 8/2006 | Linberg |
| 7,460,910 B2 | 12/2008 | Webb |
| 2002/0032470 A1 | 3/2002 | Linberg |
| 2002/0095196 A1 | 7/2002 | Linberg |
| 2003/0014090 A1 | 1/2003 | Abrahamson |
| 2003/0144711 A1 | 7/2003 | Pless et al. |
| 2004/0039651 A1 | 2/2004 | Grunzig et al. |
| 2005/0204134 A1 | 9/2005 | Von Arx et al. |
| 2006/0189854 A1 | 8/2006 | Webb et al. |

FOREIGN PATENT DOCUMENTS

| | | |
|---|---|---|
| DE | 100 52 644 A1 | 5/2001 |
| DE | 100 45 924 A1 | 4/2002 |
| EP | 1 075 161 A | 2/2001 |
| WO | WO 01/03575 A | 1/2001 |
| WO | WO 2006/029425 A | 3/2006 |

OTHER PUBLICATIONS

Amine, B., "Authentifizierung and Identitätsmanagement" Internet Article. Sicherheit und Technischer Datenschutz in Informationissystem. Seminar I, Sommersemester 2006 AM IPD—Lehrstuhl Prof. Böhm, [Online] Jun. 26, 2006, Seiten 1-18, XP002501955 Gefundem im Internet: URL:http://www.ipd.uka.de/{00sem/SecIS06/Ausarbeitungen/Seminarausarbeitung-Benchaalal-AuthentifizierungundIdManagement.pdf> [gefundem am Oct. 29, 2008].

Ueckert F. et al., "Empowerment of patients and communication with health care professionals through an electronic health record" International Journal of Medical Informatics, Elsevier Scientific Publishers, Shannon, IR, Bd. 70, Nr 2-3, (Jul. 1, 2003), Seiten 99-108 XP004444247, ISN: 1386-5056.

Koopmann G., Mobile Transaktionsnummern (TAN), IP.COM Journal, IP.COM Inc., West Henrietta, NY, US, Jul. 23, 2003.

European Search Report for European Patent Application No. 08159444.2-2201 / 2031532, Jul. 17, 2009.

*Primary Examiner* — Scott Getzow
*Assistant Examiner* — Amanda Patton
(74) *Attorney, Agent, or Firm* — Craig A. Fieschko, Esq.; DeWitt Ross & Stevens S.C.

(57) ABSTRACT

The invention comprises a system for the secure remote programming of an implant. A TAN server is provided for this purpose, in which a user is first accredited and which then generates a TAN upon a request and provides it to the user on one hand and to a patient intermediate device assigned to the implant to be reprogrammed on the other hand.

10 Claims, 2 Drawing Sheets

SYSTEM AND METHOD FOR THE REMOTE PROGRAMMING OF A PERSONAL MEDICAL DEVICE

FIELD OF THE INVENTION

The invention relates to a system and a method for the remote programming of a personal medical device, in particular an implantable medical device, such as a cardiac pacemaker, a defibrillator, or the like.

BACKGROUND OF THE INVENTION

It is known to transmit medical, physiological, or operational data obtained from a cardiac pacemaker or defibrillator to a central service center to analyze the data, and to provide it to an attending physician via a corresponding user interface.

Some functions of such implants are controlled by software or firmware and are therefore programmable. It frequently happens that after initial programming shortly before, during, or after the implantation, further programming or reprogramming is desirable to be able to adjust the implant to current health states of a patient, which have possibly changed in the meantime, or to increase the performance capability of the implant in another manner. Programming or reprogramming of this type frequently occurs by a physician's use of a short-range wireless data connection to a particular implant with the aid of a programming device and programs the implant in consideration of the patient.

However, programming or reprogramming of the implant may also fundamentally be performed remotely, for example, via the central service center. A data link may be produced for this purpose between the service center and a patient intermediate device, which is typically located in proximity to a patient and may produce a bidirectional data link between the implant and the patient intermediate device. The connection between service center and patient intermediate device may be implemented as a separate wireless connection, for example, via the telephone network, the Internet, or similar data lines.

The problem exists in this case of ensuring that the particular implant and/or the patient intermediate device is not reprogrammed as a result of an erroneous data transmission or even by misuse.

To solve this problem, encrypting and/or verifying programming instructions for the programming or reprogramming of an implant using a public-key encryption method, such as PGP, is provided according to U.S. Pat. No. 6,442,432.

SUMMARY OF THE INVENTION

The present invention allows verification that a programming instruction to a personal medical device, such as an implant or a patient intermediate device, is authentic and originates from an authorized source.

The invention can achieve verification by use of at least one additional transaction number (TAN) server as a component in addition to the personal medical device. This TAN server has a databank, which communicates entries assigned to one another to one user identification, at least one device identification, and at least one messaging address in each case. The user identification identifies a user, such as a physician. The device identification identifies a personal medical device assigned to the user, for example, attended by a physician, such as an implant or patient intermediate device. The messaging address is the address, such as the telephone number or e-mail address, of an addressable personal communication device such as a mobile telephone, a fax device, or an e-mail client. The TAN server additionally has a TAN user interface, which is implemented to accept inputs of a user and assign the inputs to a user identification and to relay them assigned in this manner to the TAN server. Moreover, the TAN server has a messaging interface, via which the TAN server may transmit a message to an addressable communication device (fax, e-mail client, mobile telephone (SMS)) of a user, which is identified by its messaging address. A further component of the TAN server is a data communication interface for an at least indirect connection for transmitting data to the programmable personal medical device.

The transaction number (TAN) server is implemented to receive a TAN request assigned to a user identification and subsequently generate a TAN message. The TAN message contains a unique transaction number (TAN) for authentication of a transaction, such as the reprogramming of the personal medical device. The TAN server transmits this TAN message via the messaging interface to the communication device assigned to the user identification of the requesting user via the databank entries and via the data communication interface to a personal medical device assigned to the user identification by the databank entries and possibly selected by the user and identified by its device identification.

The programmable personal medical device has at least one data communication interface for at least indirect connection of the personal programmable device to the transaction number (TAN) server and a TAN memory to store a TAN received on the part of the TAN server. The programmable personal medical device is implemented to store a TAN received on the part of the TAN server in the TAN memory.

It is ensured by a system of this type that a transaction number (TAN) is provided to a person assigned to a personal medical device, i.e., in particular a patient intermediate device or an implant, which is also simultaneously stored in the personal medical device. Only the TAN itself is transmitted, so that a receiver which intercepts the TAN sent to the user, for example, does not know which personal medical device it belongs to.

The security of the system may be increased if the transaction number (TAN) server is also implemented, for the purposes of accreditation of a user, to firstly receive a user identification and a messaging address of a communication device via the TAN user interface and then to transmit a message of a communication device. The TAN server is also implemented for the purpose of receiving a message via the TAN user interface and comparing this message to the message transmitted to the communication device and, if they correspond, storing the user identification together with the messaging address of the communication device as entries assigned to one another in the databank. A user who wishes to be accredited with the TAN server must therefore transmit his user identification together with an address of a communication device to the TAN server. To verify user and address of the communication device (messaging address), the TAN server then sends a message to the communication device. The user must transmit this message to the TAN server again to terminate the accreditation. If the message transmitted by the user together with a user identification to the TAN server corresponds to the buffered message previously transmitted to the user via the communication device assigned to his user identification, the user is accredited at the TAN server via his user identification and the associated messaging address of a communication device and may later perform a TAN request as described above.

After the transaction number (TAN) request, the user has a valid TAN in hand, which is simultaneously stored in the personal medical device to be programmed.

The transaction number (TAN) user interface of the TAN server is preferably executable on a computer spatially remote from the TAN server and connected via a data network to the TAN server. In this manner, it is possible to provide a central TAN server.

The system preferably has a service center different from the transaction number (TAN) server as a further component. On one hand, it has a data communication interface for a data communication with the personal medical device. A further service user interface connected to the service center is implemented in such a manner that it allows programming instructions for the programmable personal medical device to be compiled, dispatching of a compiled programming instruction to be triggered and a manual request for a TAN for a programming instruction to be requested, and a corresponding accepted TAN to be appended to a programming instruction. Furthermore, the service center is implemented to transmit a released and/or dispatched programming instruction together with a TAN released via the service user interface to the personal medical device. The personal medical device— i.e., the programming device or the patient intermediate device—is implemented for the purpose of comparing a stored TAN previously received on the part of the TAN server to a TAN received together with a programming instruction on the part of the service center and only to execute the programming instruction or relay it to an implant, for example, if both TAN are identical.

The service user interface may be implemented as a remote programming application or be connected to a remote programming application, which may be executed on a remotely executable device. The remote programming application may thus be installed on the computer of a physician, for example.

The service user interface is preferably implemented in such a manner that it may accept a transaction number (TAN) request of a user together with the user identification of this user. The service center has a second data communication interface, which is implemented to allow a data exchange from the service center to the TAN server. The service center is implemented to relay a TAN request intercepted via the service user interface to the TAN server. The user thus does not need to direct the TAN request directly to the TAN server, but rather may generate and dispatch the TAN request together with a programming instruction via the service user interface. Similarly, the TAN user interface may be connected to a TAN server application, which is also executable remotely from the TAN server and allows a user to input a TAN request together with his user identification from his own computer and have it sent to the TAN server.

The sequences presented here for the accreditation of the user on the TAN server, for the request to receive a TAN and its generation, and finally the TAN-protected remote programming of an implant are subjects of methods which also represent a solution of the object cited at the beginning.

BRIEF DESCRIPTION OF THE DRAWINGS

The invention will be explained in greater detail on the basis of an exemplary embodiment with reference to the figures. In the figures.

DETAILED DESCRIPTION OF PREFERRED VERSIONS OF THE INVENTION

Figure 1:
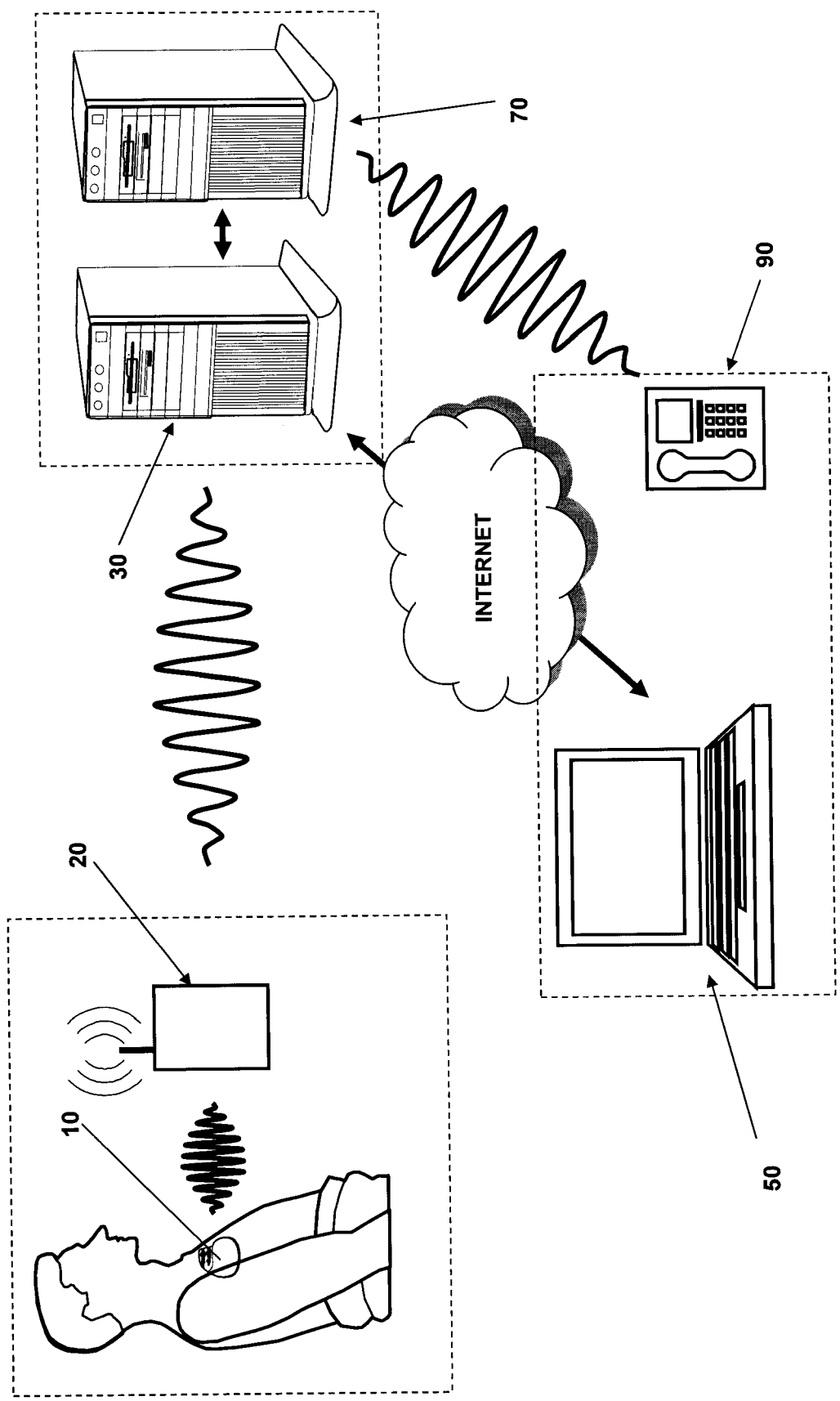
FIG. 1: shows a system for the remote programming of an implant.
Figure 2:
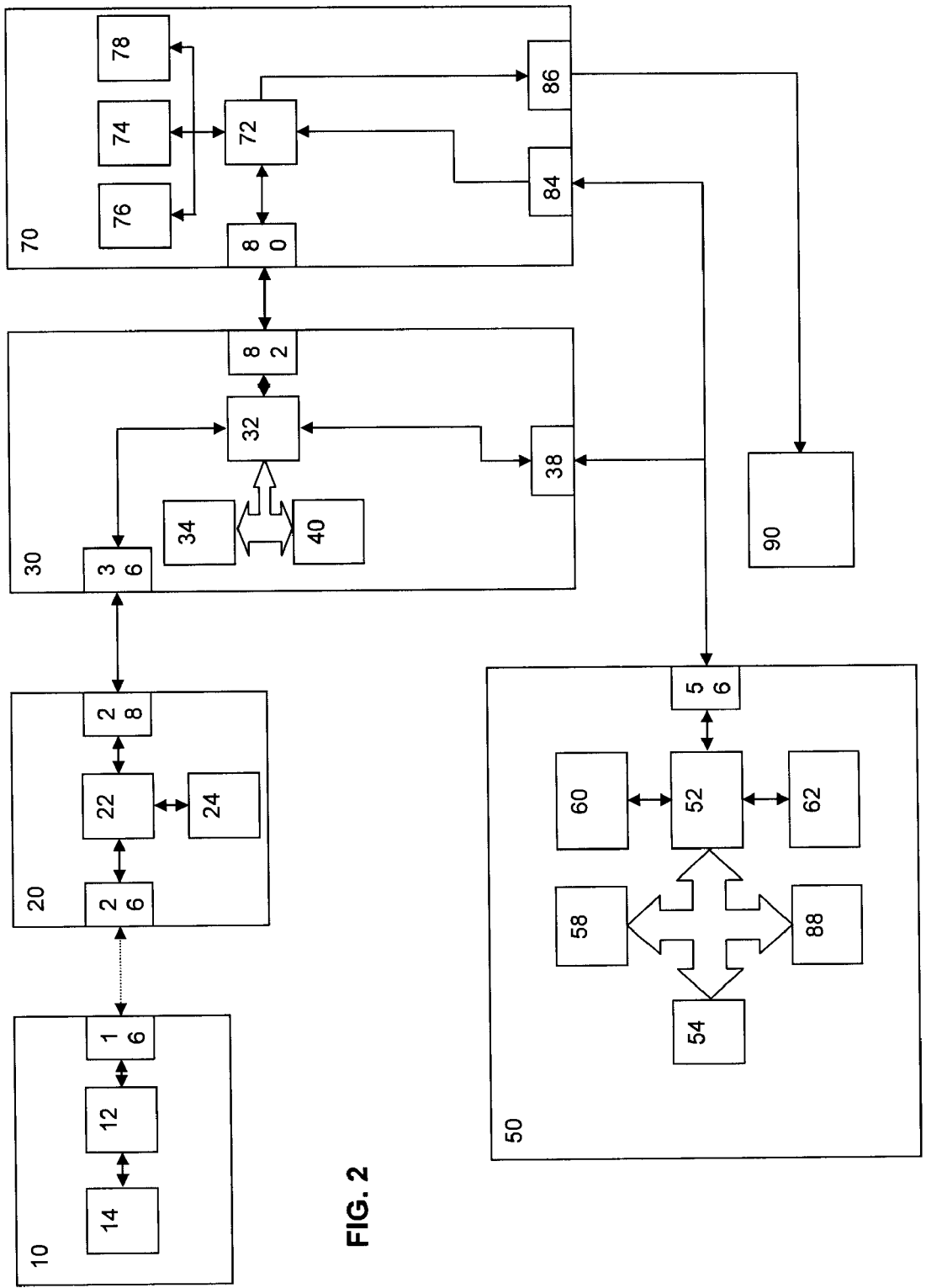
FIG. 2: shows block diagrams of the components of the system of FIG. 1.

FIG. 1 shows the components of an exemplary system for the remote programming of implants. One component is the implant 10 itself. It has a controller 12 (see FIG. 2), which is connected to both a memory 14 and also a telemetry unit 16. The telemetry unit 16 allows a wireless, bidirectional data transmission from and to the implant 10.

A further component is a patient intermediate device 20, which also has a controller 22, which is connected to a memory 24 and a first data communication interface 26 for a bidirectional data transmission from and to the implant 10, and to a second data communication interface 28, via which the patient intermediate device 20 may exchange data with a central service center 30 bidirectionally.

In addition to a controller 32, the central service center 30 has a central databank 34 and a first data communication interface 36, via which the service center 30 may exchange data with the patient intermediate device 20 bidirectionally. In addition, the central service center 30 has a remote programming server unit 40, which is connected to both the control unit 32 of the service center 30 and also to an Internet interface 38 for connecting a remote programming client 50.

The remote programming client 50 also has a central control unit 52, which is connected to a memory 54 and a data communication interface 56 for bidirectional data communication with the service center 30. In addition, the remote programming client 50 has a remote programming application 58, which may be executed with the aid of the central control unit 52 and the memory 54 and is either executable as a stand-alone solution exclusively on the remote programming client 50 or partially or entirely also uses the central service center 30 and its remote programming server unit 40 as a server application. The remote programming application 58, display 60, and input unit 62 form a service user interface which is connected via the Internet interface 38 to the service center 30.

The remote programming application 58 allows programs to be compiled on the remote programming client 50, which are executable for the implant 10 and its controller 12. The programs thus compiled may be transmitted in the form of a programming instruction from the central service center 30 via the patient intermediate device 20 to the implant 10.

To display images generated by the remote programming application 58, the remote programming client 50 has a display 60. In addition, an input unit 62 is provided so that a user, such as a physician, may make inputs for the remote programming of the implant 10.

The implant 10 (in any case) and the patient intermediate device 20 are spatially located in proximity to a patient. The central service center 30 is situated at a central location. The remote programming client 50 is located in proximity to a physician and may be very remote from the service center 30.

Further components of the system for TAN-protected remote programming of a medical implant are a TAN server 70 independent of the service center 30, as well as a personal communication device 90, such as an e-mail client, a mobile telephone, or a fax device of a physician, which may receive messages transmitted on the part of the TAN server 70.

The TAN server 70 has a TAN server control unit 72, which is connected to both a databank 74 and also to a TAN generator 76 and a comparison unit 78. A data communication interface 80 allows the data exchange with the service center 30, which has a corresponding data interface 82. A further data communication interface 84 allows the bidirectional data exchange with a personal computer of a physician, in particular with the remote programming client 50. Finally, a third data communication interface 86 is provided, via which the TAN server 70 is connected to the communication device 90. The third data communication interface 86 forms a messaging interface for the invention.

In addition, a TAN server application 88 is installed on the remote programming client 50, which allows access to the TAN server 70 from the remote programming client 50. The TAN server application 88, the display 60, and input unit 62 form a TAN user interface which is connected via the data communication interface 84 to the TAN server 70.

The memory 24 of the patient intermediate device 20 is implemented to store a TAN received directly from the TAN server 70 or—as in the case shown—using the service center 30. The controller 22 of the patient intermediate device 20 is additionally implemented to compare a TAN stored in the memory 24 with a TAN in a received programming instruction and only to relay a received programming instruction to the implant 10 if both TAN correspond.

The TAN server 70 is provided for the secure generation of a TAN of this type.

A user who wishes to remotely program the implant 10 must first be accredited with the TAN server 70. For this purpose, he uses the TAN server application 88 on the remote programming client 50 and inputs his user identification together with the messaging address for his personal communication device 90. The TAN server 70 then generates a test message and transmits it to the messaging address previously sent to it. A physician may now input this messaging address together with his user identification via the TAN server application 88 and transmit a corresponding message to the TAN server 70. In the TAN server 70, the comparison unit 78 compares the previously dispatched message to the recently received message and, in case of correspondence, causes the user identification to be stored, together with the messaging address and a device identification which identifies a patient intermediate device 20, assigned to one another in the databank 74. In this case, the corresponding user is accredited with the TAN server 70. If the dispatched message and the message transmitted back do not correspond, the corresponding user is not registered using corresponding entries in the databank 74.

For the purposes of remote programming of the implant 10, a physician must retrieve a TAN at the TAN server 70 and prepare a programming instruction. This may either be performed via the remote programming application 58 in that the TAN request is first transmitted to the service center 30 and then transmitted therefrom via the data interface 82 and the data communication interface 80 to the TAN server 70. Alternatively thereto, the TAN request may also be performed directly via the TAN server application 88 at the TAN server 70.

After receiving a TAN request, the TAN generator 76 of the TAN server 70 generates a TAN and causes it to be transmitted on one hand to the patient intermediate device 20, which stores the TAN in the memory 24. On the other hand, the TAN is transmitted via the data communication interface 86 to the communication device 90.

A physician who compiles a programming instruction for the implant 10 with the aid of the remote programming client 50 and the remote programming application 58 may append the TAN received on the part of the communication device 90 to the programming instruction and transmit it via the service center 30 to the patient intermediate device 20.

The patient intermediate device 20 compares the TAN received together with the programming instruction to the TAN previously transmitted on the part of the TAN server 70 and stored in the memory 24. If the two TAN correspond, the programming instruction is relayed to the implant 10.

The system thus comprises the following components:

(1) A TAN server 70, physically, administratively, and organizationally separate from the server(s) forming the actual service center 30, used by a separate, separately executable TAN server application 88.

(2) The service center 30, accessible via a remote programming application 58, which is also executable on a remote programming client 50 remote from the service center 30, such as a physician's computer.

(3) The patient intermediate device 20 (mobile device, CardioMessenger) in proximity to the patient.

(4) The remotely-programmable implant 10, implanted in the patient.

Remote programming of the implant 10 using this system is executed as follows. Firstly, a physician is accredited for remote programming:

1. Simultaneously with the receipt of a user identification for the service center 30, each user (physician) receives the possibility of accrediting himself separately on a TAN server 70 existing especially for remote programming (re-programming from a distance) and storing a messaging address (mobile telephone number, e-mail address, or a fax address or the like) therein.

2. If the physician selects this possibility and stores a mobile telephone number, e-mail address, or fax number, he receives a test message transmitted there, which he must transmit via a TAN server application 88 to the TAN server 70 for verification. Only then is the stored messaging address valid.

This physician may subsequently reprogram the implant 10:

3. As soon as the physician now sees the necessity of reprogramming an implant 10 remotely, he activates the remote programming application 58, selects the implant 10 to be reprogrammed using this application, and signals that he requires a mobile TAN. He generates this signal either in the remote programming application 58 (which relays it via the service center 30 to the TAN server 70) or in the TAN server application 88 itself.

4. The TAN server 70 now transmits a random TAN to the patient intermediate device 20, and/or to the device address which the physician has stored for himself in the TAN server 70.

5. The remote programming application 58 now requests the TAN which the physician has received on his communication device 90 to confirm the remote reprogramming of the implant 10.

6. This TAN is appended to the programming instruction (data packet) which contains the reprogramming instructions for the implant 10.

7. The programming instruction is then transmitted by the service center 30 to the patient intermediate device 20.

8. Upon receiving the programming instruction, the patient intermediate device 20 checks whether the TAN contained therein is the same which it has received from the TAN server 70.

9. If so, the patient intermediate device 20 transmits the programming instruction further to the implant 10. Otherwise, it discards the programming instruction.

What is claimed is:

1. A method for the remote programming of a programmable personal medical device (10, 20), the method including the steps, within a transaction number (TAN) server (70), of:
   a. receiving a TAN request containing a device identification and a user identification;
   b. generating a TAN;
   c. transmitting the generated TAN to:
      (1) a programmable personal medical device (10, 20) identified by the device identification, and
      (2) a messaging address of a communication device (90) of a user corresponding to the user identification; and
   d. accrediting a user by:
      (1) receiving a user identification and a messaging address from a user;
      (2) transmitting a test message to the messaging address of the user;
      (3) receiving a response message from the user;
      (4) comparing the transmitted test message to the received response message; and
      (5) if the response message corresponds to the test message, authenticating the user, whereby the user identification and messaging address are stored in association.

2. The method of claim 1 wherein, if the user is authenticated, the user identification and messaging address are stored in association in a databank (74) associated with the TAN server (70).

3. The method of claim 1 wherein the TAN is generated only if the user is authenticated.

4. The method of claim 1 wherein:
   a. the user identification and the messaging address are received by the TAN server (70) from a TAN user interface (88, 60, 62); and
   b. the response message from the user is received by the TAN server (70) from the TAN user interface (88, 60, 62).

5. The method of claim 4 wherein the TAN user interface (88, 60, 62):
   a. receives the messaging address from the user, and
   b. assigns the user identification to the messaging address.

6. The method of claim 1 further including the steps of:
   a. receiving programming instructions from a user in association with a TAN;
   b. executing the programming instructions in the programmable personal medical device (10, 20) only if the associated TAN corresponds to the generated TAN transmitted to the programmable personal medical device (10, 20).

7. The method of claim 6 wherein:
   a. a service center (30) has a first data communication interface (36) in communication with the programmable personal medical device (10, 20), and
   b. a service user interface (88, 60, 62) is in communication with the service center (30), wherein the service user interface (88, 60, 62):
      (1) compiles the programming instructions from the user,
      (2) requests a TAN for the compiled programming instructions, and
      (3) transmits the compiled programming instructions with the TAN to the programmable personal medical device (10, 20).

8. A method for the remote programming of a programmable personal medical device (10, 20),
   a. the method including the steps, within a transaction number (TAN) server (70), of:
      (1) receiving a TAN request containing a device identification and a user identification;
      (2) generating a TAN; and
      (3) transmitting the generated TAN to:
         (i) a programmable personal medical device (10, 20) identified by the device identification; and
         (ii) a messaging address of a communication device (90) of a user corresponding to the user identification;
   b. wherein the programmable personal medical device (10, 20) includes:
      (1) a data communication interface (28) in communication with the TAN server (70), wherein the TAN generated by the TAN server (70) is received by the data communication interface (28);
      (2) a TAN memory (14, 24) storing the TAN received from the TAN server (70), and
      (3) a programmable controller (12, 22) at least partially defining the functionality of the programmable personal medical device (10, 20), wherein the programmable controller (12, 22) executes programming instructions received from a user if the programming instructions are received in association with a TAN corresponding to the generated TAN transmitted to the programmable personal medical device (10, 20).

9. A method for the remote programming of a programmable personal medical device (10, 20),
   a. the method including the steps, within a transaction number (TAN) server (70), of:
      (1) receiving a TAN request containing a device identification and a user identification;
      (2) generating a TAN; and
      (3) transmitting the generated TAN to:
         (i) a programmable personal medical device (10, 20) identified by the device identification; and
         (ii) a messaging address of a communication device (90) of a user corresponding to the user identification;
   b. wherein the TAN server (70) includes:
      (1) a databank (74) having entries including:
         (i) a user identification identifying a user,
         (ii) a device identification identifying a programmable personal medical device (10, 20), the device identification being associated with the user identification, and
         (iii) a messaging address of an addressable communication device (90), the messaging address being associated with the user identification;
      (2) a messaging interface (86) in communication with one or more addressable communication devices (90), wherein upon receipt of a TAN request from a user, the TAN server (70) transmits the generated TAN via the messaging interface (86) to the addressable communication device (90) having the messaging address associated with the user's user identification in the databank (74); and
      (3) a data communication interface (80) in communication with one or more personal medical devices (10, 20), wherein upon receipt of a TAN request from a user, the TAN server (70) transmits the generated TAN via the data communication interface (80) to the programmable personal medical device (10, 20) having the device identification associated with the user's user identification in the databank (74).

10. A method for the remote programming of a programmable personal medical device (10, 20), the method including the steps, within a transaction number (TAN) server (70), of:
   a. receiving a TAN request containing a device identification and a user identification;
   b. generating a TAN;
   c. transmitting the generated TAN to:
      (1) a programmable personal medical device (10, 20) identified by the device identification; and
      (2) a messaging address of a communication device (90) of a user corresponding to the user identification;
   d. obtaining the TAN request and the device identification from a user at a TAN user interface (88, 60, 62), the TAN user interface (88, 60, 62) assigning the user identification to the TAN request and the device identification; and
   e. relaying the TAN request, the device identification, and the assigned user identification to the TAN server (70).

* * * * *